United States Patent [19]

Yensen

[11] Patent Number: Plant 6,461

[45] Date of Patent: Dec. 13, 1988

[54] SALTGRASS PLANT NAMED YENSEN 1

[75] Inventor: Nicholas P. Yensen, Tucson, Ariz.

[73] Assignee: Salt Weeds, Tucson, Ariz.

[21] Appl. No.: 901,315

[22] Filed: Aug. 28, 1986

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Cahill, Sutton & Thomas

[57] ABSTRACT

A variety of *Distichlis palmeri*, characterized by vigorous growth in salty soils, high grain yield and ideal form for harvest, and for human consumption.

2 Drawing Sheets

DESCRIPTION

The presently described plant is related to the grain and plants described in copending applications for plant patent filed by the present inventor entitled "Yensen 2" and "Yensen 3", assigned to the present assignee, filed concurrently herewith on Aug. 28, 1986, assigned Ser. Nos. 901,316 and 901,204, respectively.

The present invention relates to a new and distinct variety of a plant of the family Poaceae and more particularly to a plant of the species *Distichlis palmeri* (Vasey) Fassett ex I. M. Johnston, commonly known as salt grass and is a perennial herbaceous flowering plant.

The accompanying drawings comprise color photographs of my new variety of salt grass:

This new variety was discovered at test plots of Salt Weeds (an Arizona partnership) in Tucson, Ariz.

The new variety was noted in test plantings wherein approximately 100,000 seeds, seedlings and cuttings have been test planted under agricultural conditions on a total of 2.5 acres following over ten (10) years of study of salt-tolerant plants. The purpose of these large plantings was specifically to discover new varieties with crop potential and to learn their agronomic requirements. The new variety resulted from a bed seedling.

Wild plants of *Distichlis palmeri* produce from near zero to four grams of grain per square meter. Yensen 1 can produce well over ten grams of grain per square meter. The optimum yields with respect to fertilizer and water levels of Yensen 1 are not known at this time.

The new variety was first noted for its vigorous growth and ideal form and later for its high yield of grain on relatively short stalks. The stalks are erect and the grain heads are of a suitable height for combine harvest.

The new variety is being reproduced via rhizomes in Tucson, Ariz., where a number of other varieties are also being observed.

Figure 1:
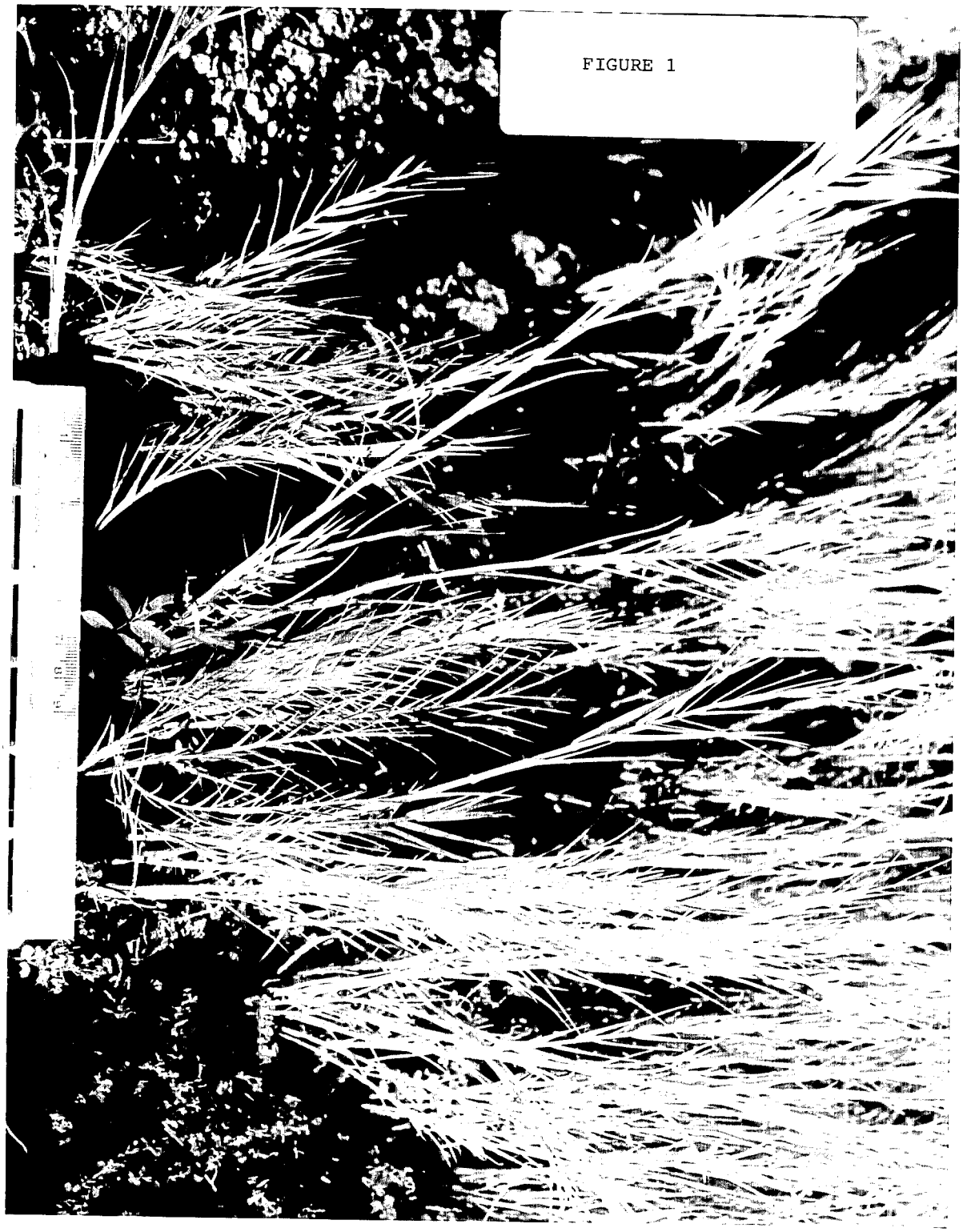
FIG. 1 is a photograph of my new salt grass.

The new variety has a number of characteristics and desirable features distinguishing it as an improved variety. These characteristics are principally the vigorous growth, high yield and ideal form suitable for harvest (see FIG. 1).

The following is a detailed description of the new variety:

Parentage: A seedling from "in house" harvested caryopses (seeds) of *Distichlis palmeri.*

Propagation: To date all rhizome shoots have held true to the distinguishing characteristics of the initial shoots and it is expected that plants from caryopses will also hold true to the distinguishing characteristics of the initial shoots as described herein.

Figure 2:
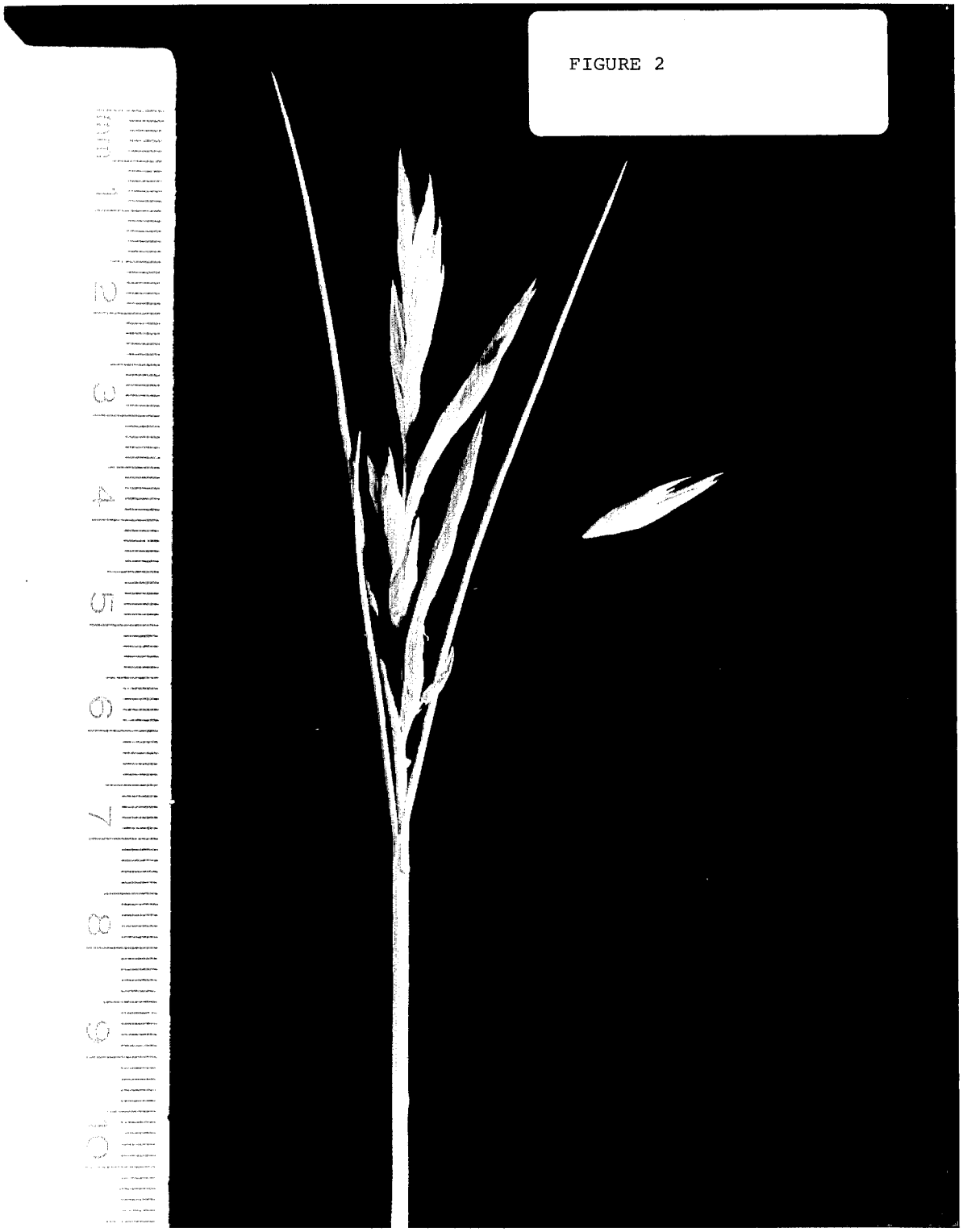
FIG. 2 is a photograph of the culm and caryopses of my new salt grass.

Culms: Rigid, erect, occasionally branched, glabrous, 20–50 cm high depending on rhizome age at inflorescence, 2–3 mm in diameter (see FIG. 2).

Rhizomes: Thick and scaled at nodes.

Blades: Firm, rigid, ascending, pointed and pungent, involute (especially upon drying), distichous, glabrous to slightly puberulent, 3–5 MM basal width, 20–30 veins at base, typically 30–80 mm in length.

Sheath: Glabrous to slightly puberulent, with a tuft of wooly hairs at either side of the mouth, ligule smooth with pubescence apically.

Inflorescence:

*Panicle.*—Erect, compoundly branched (often branched in two's), 4–8 cm in length and does not extend beyond the leaves.

*Spikelet.*—With 5–9 flowers, subtending "bracts" infertile, 20–40 mm in length, 6–10 mm in width.

*Florets.*—Lemma 10–15 in length decreasing slightly apically on the spikelet, 4–6 feint veins on either side of a weak keel. Palea 9–11 mm in length, length decreasing slightly apically on the spikelet.

*Caryopsis.*—6–11 mm in length (including the bifurcated style), length decreasing slightly apically on the spikelet, 1–2 mm in width, 1–2 mm in height; embryo cover 2–4 mm in length; ventral surface indented with a longitudinal groove (except in unusually well-filled caryopses); anterior seed coat longitudinally wrinkled and posterior portion wrinkled into two rounded ventral keels and one rounded dorsal keel which extends to the bifurcation of the styles; surface texture with numerous longitudinal striae and light vertical rugae, glabrous, colored a coriaceous brown and tends to be darker anteriorly and lighter posteriorly.

I claim:

1. A new and distinct plant variety *Distichlis palmeri* as shown and described, which is principally characterized by vigorous growth, high grain yield and ideal form for harvesting.

* * * * *